(12) United States Patent
Goldfinger

(10) Patent No.: US 7,671,083 B2
(45) Date of Patent: Mar. 2, 2010

(54) P-ALKOXYPHENYLEN-THIOPHENE OLIGOMERS AS ORGANIC SEMICONDUCTORS FOR USE IN ELECTRONIC DEVICES

(75) Inventor: Marc B. Goldfinger, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 381 days.

(21) Appl. No.: 11/660,797

(22) PCT Filed: Aug. 23, 2005

(86) PCT No.: PCT/US2005/030289

§ 371 (c)(1),
(2), (4) Date: Feb. 21, 2007

(87) PCT Pub. No.: WO2006/024012

PCT Pub. Date: Mar. 2, 2006

(65) Prior Publication Data

US 2007/0290198 A1    Dec. 20, 2007

(51) Int. Cl.
*A61K 31/381* (2006.01)
(52) U.S. Cl. ...................................... 514/444
(58) Field of Classification Search .................. 514/444
See application file for complete search history.

(56) References Cited

U.S. PATENT DOCUMENTS

| 4,861,692 A | 8/1989 | Kuroda et al. |
| 6,452,207 B1 | 9/2002 | Bao |

FOREIGN PATENT DOCUMENTS

JP      2004 165257      6/2004

OTHER PUBLICATIONS

King, Med. Chem: Principle and Practice (1994), pp. 206-208.*
S. R. Bayly et. al., Electronic and Magnetic Metal -Metal Interactions in Dinuclear Oxomolybdenum (v) Complexes Across Bis-Phenolate Bridging Ligands With Different Spacers Between the Phenolate Termini: Ligand-Centred vs. Metal-Centred Redox Activity, Journal of Chemical Society, Dalton Transactions, 2001, vol. 9:1401-1414.
Hisao Yanagi et. al., Comparative Carrier Transport Characteristics in Organic Field Effect Transistors With Vapor Deposited Thin Films and Epitaxially Grown Crystals of Biphenyl-Capped Thiophene Oligomers, Adv. Funct. Mater., 2003, vol. 13:767-773.
Melissa Mushrush et. al., Easily Processable Phenylene Thiophene Based Organic Field Effect Transistor and Solution Fabricated Non-volatile Transistor Memory Elements, J. Am. Soc., 2003, vol. 125:9414-9423.
Bert De Boer et. al., Synthesis and Characterization of Conjugated Mono and Dithiol Oligomers and Characterization of Their Self Assembled Monolayers, Langmuir, 2003, vol. 19:4272-4284.
Howard E. Katz et. al., Design of Organic Transistor Semiconductors for Logic Elements, Displays, and Sensors. Proceedings of SPIE, The International Society for Optical Engineering, 2001, vol. 4466:20-30.

* cited by examiner

*Primary Examiner*—Taofiq A Solola
(74) *Attorney, Agent, or Firm*—Gail D. Tanzer

(57) ABSTRACT

This invention provides phenylene-thiophene compounds that exhibit useful electronic properties such as high mobility and high on/off ratio. The invention also provides electronic devices incorporating these compounds. These devices include field effect transistors (FETs), thin film transistors (TFTs), display devices, light-emitting diodes, photovoltaic cells, photo-detectors, and memory cells. Further, the invention also describes a method for manufacturing these field effect transistors. The invention describes an electronic device comprising one or more compounds represented by Formula: (I) where R is selected from substituents comprising 1-20 carbon atoms, wherein the substituents are selected from substituted or unsubstituted alkyl groups, substituted or unsubstituted alkenyl groups, and substituted or unsubstituted alkynyl groups; n is an integer selected from 2 through 6; and m and m' are integers selected independently from 1 through 3.

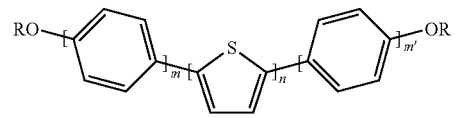

12 Claims, 1 Drawing Sheet

P-ALKOXYPHENYLEN-THIOPHENE OLIGOMERS AS ORGANIC SEMICONDUCTORS FOR USE IN ELECTRONIC DEVICES

FIELD OF THE INVENTION

This invention provides a new class of phenylene-thiophene compounds. The invention also provides electronic devices incorporating the new phenylene-thiophene compounds.

BACKGROUND OF THE INVENTION

Many organic materials have been used in electronic devices. The use of organic materials for the fabrication of electronic devices such as field-effect transistors (FETs) has been studied in great detail and many organic substances that display interesting electronic properties have been synthesized. These materials provide low-cost integrated circuit (IC) technology suitable for applications such as smart cards, electronic tags, displays, and memory devices.

U.S. Pat. No. 6,452,207 discloses a class of fluorene oligomer compounds and describes a thin film transistor device that comprises a semiconductor layer of fluorene oligomer compounds. These fluorene oligomers are deposited by simple evaporation to achieve desirable semiconductor properties.

Other organic compounds that have been investigated for use as semiconductors include regioregular poly(3-alkylthiophene)s, oligothiophene derivatives, and fused aromatic compounds such as pentacene and tetracene. These compounds have also been found to exhibit semiconductor properties.

However, most of the above organic semiconductors compounds are p-channel. They possess a relatively high HOMO (highest occupied molecular orbital) energy level and are easily oxidized. This results in poor device stability and makes these compounds unsuitable for practical electronic circuit applications. Moreover, these compounds often exhibit high oxygen and moisture sensitivity, leading to poor on/off current ratios and limited environmental stability.

Furthermore, the synthesis of many of these compounds is low yielding. This leads to problems in purification of these compounds. Impurities present in these compounds, in turn, can lead to difficulties in achieving long range molecular ordering. This adversely affects the semiconductor properties such as field effect mobility and on/off current ratio.

Some phenylene-thiophene compounds, when used in electronic devices, are highly stable and remain unaffected by heat, air, or light. They also provide high field-effect mobility and high on/off ratio. A method for the preparation of some phenylene-thiophene compounds has been disclosed by S. R. Bayly, et al., *Journal of the Chemical Society*, Dalton Transactions, 2001, Volume 9, pp. 1401-1414. This publication describes electronic and magnetic metal-metal interactions in dinuclear oxomolybdenum (V) complexes and the dependence of these interactions on the nature of bridging ligands. The bridging ligands mentioned in this publication include some phenylene-thiophene compounds. However, the publication does not mention any other use of these phenylene-thiophene compounds, for instance, in electronic devices.

Despite the continuing interest in using organic semiconductors in electronic devices, there still exists a need for a class of organic compounds that have high mobility and high on/off ratio, and are stable to heat, light, and air. Furthermore, there is a need for organic compounds that can be readily prepared in high yield, easily purified, and incorporated into electronic devices using commercially viable fabrication methods.

SUMMARY OF THE INVENTION

One aspect of this invention is an electronic device comprising one or more phenylene-thiophene compounds having Formula 1:

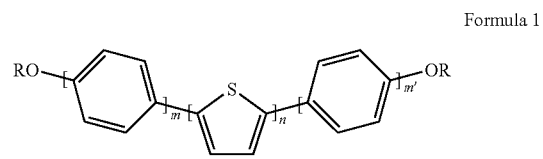

Formula 1 where R is selected from substituents comprising 1-20 carbon atoms, wherein the substituents are selected from substituted and unsubstituted alkyl groups, substituted and unsubstituted alkenyl groups, and substituted and unsubstituted alkynyl groups;

n is an integer of 2 through 6; and m and m' are integers selected independently from 1 through 3.

Another aspect of the present invention is phenylene-thiophene compounds having Formula 1A:

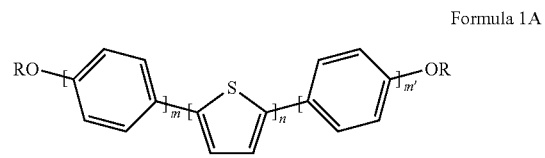

Formula 1A where R is selected from substituents comprising 2-20 carbon atoms, wherein the substituents are selected from substituted and unsubstituted alkyl groups, substituted and unsubstituted alkenyl groups, and substituted and unsubstituted alkynyl groups;

n is an integer of 2 through 6; and m and m' are integers selected independently from 1 through 3.

A further aspect of the present invention is an electronic device comprising an organic field-effect transistors (FET), incorporating the phenylene thiophene compounds of Formula 1.

Another aspect of the present invention is a process for manufacturing electronic devices comprising an organic field-effect transistors (FET), incorporating the phenylene thiophene compounds of Formula 1.

A further aspect of the present invention is a display device comprising a phenylene thiophene compound of Formula 1.

DETAILED DESCRIPTION OF THE INVENTION

Figure 1:
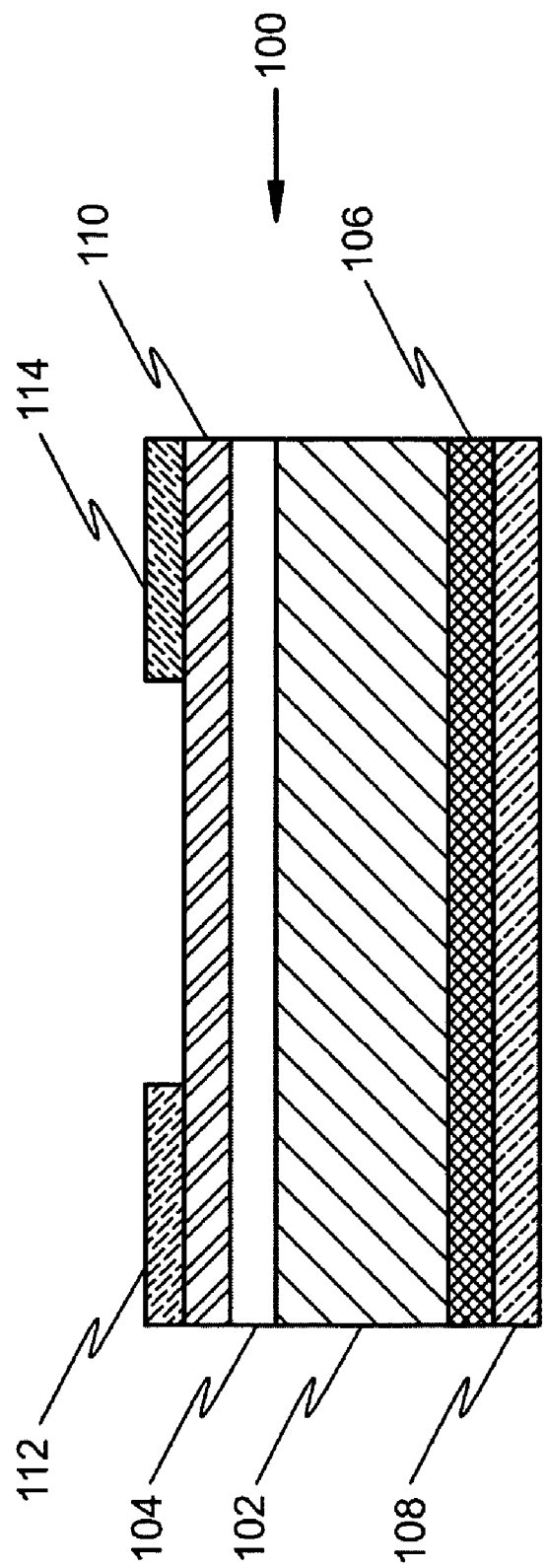
FIG. 1 is a schematic diagram of a field effect transistor (FET) device comprising a compound of Formula 1, in accordance with one embodiment of the invention.

The present invention provides a new class of phenylene-thiophene compounds. The phenylene-thiophene compounds of this invention are represented by Formula 1A:

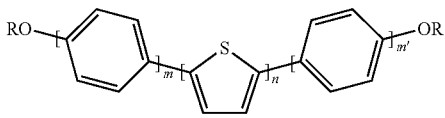

Formula 1A where R is selected from substituents comprising 2-20 carbon atoms, wherein the substituents are selected from substituted and unsubstituted alkyl groups, substituted and unsubstituted alkenyl groups, and substituted and unsubstituted alkynyl groups;

n is an integer of 2 through 6; and m and m' are integers selected independently from 1 through 3.

The phenylene-thiophene compounds exhibit high mobilities and high on/off ratios. The compounds are suitable for fabrication of semiconductor devices because of the many advantages that they offer. Firstly, these compounds have high thermal stability. Secondly, semiconductor devices fabricated from these compounds can operate without the need for an inert atmosphere and are unaffected by light or air. Thirdly, the use of these compounds allows the manufacture of electronic devices at a low substrate temperature. These compounds also have good film forming abilities.

In some embodiments, the invention includes electronic devices comprising one or more phenylene-thiophene compound shaving Formula 1:

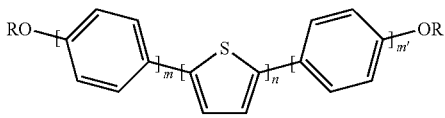

Formula 1 where R is selected from substituents comprising 1-20 carbon atoms, wherein the substituents are selected from substituted and unsubstituted alkyl groups, substituted and unsubstituted alkenyl groups, and substituted and unsubstituted alkynyl groups;

n is an integer selected from 2 through 6; and m and m' are integers selected independently from 1 through 3.

The phenylene-thiophene compounds can be used in making light-emitting diodes, photo conductors, memory cells, current limiters, field-effect diodes, Schottky diodes, photovoltaic cells, photo-detectors, thin film transistors (TFTs), rectifiers, transistors, thermistors and p-n junctions.

The term "alkyl" or "unsubstituted alkyl", whether used herein as part of another term or used independently, denotes a saturated hydrocarbon radical. Examples of alkyl groups are n-butyl, n-pentyl, n-hexyl, n-heptyl, n-octyl, iso-butyl, t-butyl, and iso-pentyl. The term 'substituted alkyl' denotes alkyl that is mono-substituted, or poly-substituted with the same or different substituent groups.

The term "alkenyl" or "unsubstituted alkenyl", whether used herein as part of another term or used independently, denotes hydrocarbon radicals having one or more double bonds between neighboring carbon atoms of the radical. Examples of the alkenyl groups are vinyl, allyl, butenyl, pentenyl, and heptenyl. The term 'substituted alkenyl' denotes an alkenyl group, which is mono-substituted, or poly-substituted with the same or different substituent groups.

The term "alkynyl" or "unsubstituted alkynyl", whether used herein as part of another term or used independently, denotes hydrocarbon radicals having one or more triple bonds between neighboring carbon atoms of the radical. Examples of alkynyl groups are ethynyl, propynyl, butynyl, hexynyl and heptynyl. The term 'substituted alkynyl' denotes an alkynyl group, which is mono-substituted, or poly-substituted with the same or different substituent groups.

Suitable substituent groups include cyanide groups, nitro groups, ester groups, ether groups, halogen substituents, hydroxy groups, substituted or unsubstituted alkyl groups, substituted or unsubstituted aryl groups, and substituted or unsubstituted alkoxy groups. Preferred substituents include ether groups and fluorine substituents.

Substituted and unsubstituted alkyl groups, alkenyl groups, and alkynyl groups can be straight chain or branched-chain. Examples of straight-chain alkyls, alkenyls, and alkynyls include n-butyl, n-pentyl, n-heptyl, n-octyl, n-butenyl, n-pentenyl, n-heptenyl, and n-heptynyl. Examples of branched-chain alkyls, alkenyls, and alkynyls include iso-butyl, t-butyl, iso-pentyl, neo-pentyl, isopentenyl, and neo-pentenyl.

Examples of the phenylene-thiophene compounds of Formula 1 include:

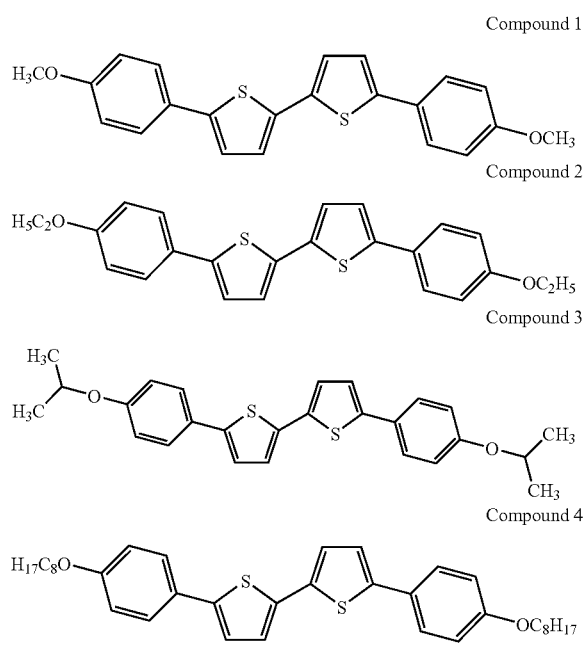

In Compound 4, The $C_8H_{17}$ group can be a straight chain or branched alkyl group. Some examples of structural groups represented by $C_8H_{17}$ are given below:

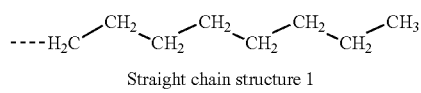

Straight chain structure 1

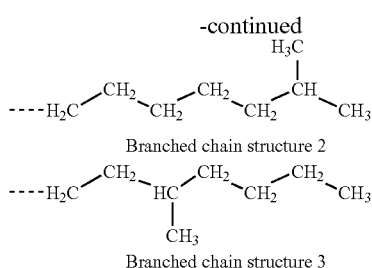

Branched chain structure 2

Branched chain structure 3

The phenylene-thiophene compounds of Formula 1 exhibit semiconductor properties such as high mobility and high on/off ratio. These properties enable the use of compounds of the phenylene-thiophene in semiconductor devices. An exemplary embodiment of the use of a compound of Formula 1 in a field effect transistor (FET) device is described below.

Brief Description of FIG. 1

FIG. 1 is a field effect transistor (FET) device comprising a phenylene-thiophene compound of Formula 1, in accordance with one embodiment of the invention. FET Device 100 is fabricated in a top contact geometry. A gate insulator layer 104 of thermal oxide is grown on one side of a heavily n-doped silicon wafer 102. A titanium adhesion layer 106 is deposited onto the other side of the wafer 102. A gold gate electrode 108 is deposited onto titanium adhesion layer 106. A compound of Formula 1 is deposited on layer 104 to form a film 110. A source electrode 112 and a drain electrode 114 complete the FET device 100.

A typical FET device corresponding to FIG. 1 that incorporates a phenylene-thiophene compound of Formula 1 can be fabricated using standard techniques, as described herein. On one side of a heavily n-doped silicon wafer 102, a gate insulator layer 104 of thermal oxide, with a thickness of 220 nm, is grown. A titanium adhesion layer 106 is evaporated onto the other side of the wafer 102. A gate electrode 108 is evaporated onto titanium adhesion layer 106. In one embodiment of the invention, the gate electrode 108 is provided by physical vapor deposition (e.g., thermal evaporation or sputtering). Gate electrode 108 can also be deposited by using inkjet printing.

Alternatively, the gate insulator layer 104 may comprise an organic material, e.g. a polymer. Exemplary gate insulators include fluorinated para-xylene, fluoropolyarylether, fluorinated polyimide, polystyrene, poly (cc-methyl styrene), poly (oc-vinylnaphthalene), poly(vinyltoluene), polyethylene, cis-polybutadiene, polypropylene, polyisoprene, poly(4-methyl-1-pentene), poly(tetrafluoroethylene), poly(chlorotrifluoroethylene), poly(2-methyl-1,3-butadiene), poly(p-xylylene), poly[1,1-(2-methyl propane), poly(cyclohexyl methacrylate), poly(chlorostyrene), poly(2,6-dimethyl-1,4-phenylene ether), polyisobutylene, poly(vinyl cyclohexane), poly(arylene ether), polyphenylene, polypropylene (preferably amorphous polypropylene), copolymers of tetrafluoroethylene and dioxoles such as 2,2-bistrifluoromethyl 5 4,5-difluoro-1,3-dioxole (available, for example from Sigma-Aldrich or E. I. DuPont de Nemours, Inc. under the tradename Teflon® AF, or from Asahi Glass under the tradename CYTOP®), fluoropolymers, fluoroepoxy polymers, fluorosilane, fluoroacrylic polymers (available, for example from Cytonix Corporation in the PFC GH, PFC GU, PFC MH product range), poly(dimethyl)siloxane and its copolymers, poly (ethylene/tetrafluoroethylene), poly (ethylene/chlorotrifluoroethylene), fluorinated ethylene/propylene copolymer, polystyrene-co-a-methyl styrene, ethylene/ethyl acrylate copolymer, poly(styrene/butadiene), poly(styrene/2,4 dimethylstyrene), polypropylene-co-1-butene, polyvinylalcohol, polyvinylphenol, polymethylmethacrylate, cyanoethylated polysaccharides such as cyanoethylpullulane, polyvinylidenefluoride, polyurethane polymers, poly(vinyl chloride/vinylacetate)polymers, poly(4-methylstyrene), and poly (1,3-butadiene). The above list is non-exhaustive and other polymers can be used.

The polymer may optionally be cross-linked after coating by heat or radiation.

The polymer may optionally contain a high permittivity additive, for example TiO2, Tarot, SrTiO, Bi4TiO, BaMgF4, barium zirconium titanate, or barium strontium titanate. These may be deposited preferably by liquid coating in the form of dispersions or by sol-gel processes.

In accordance with one embodiment of the invention, gate electrode 108 comprises gold. In other embodiments, the gate electrode 108 can comprise other conductive metals or organic conductive polymer compositions. For example, gate electrode 108 can comprise a doped-silicon, doped polyaniline, poly(3,4-ethylenedioxythiophene)/poly-(styrene sulfonate) (PEDOT:PSS), or a metal such as aluminum, chromium, silver, nickel, palladium, platinum, tantalum, or titanium. In addition, alloys, combinations, and multilayers of these materials can also be used.

Wafer 102 can be cleaned by washing it with acetone, isopropanol, water, and finally treating with oxygen plasma. A compound of Formula 1 is then thermally evaporated on layer 104 at low pressure (~$10^{-6}$ torr) to form a film 110. The rate of evaporation of compound of Formula 1 on layer 104 can range from 0.01 to 3 Å/s. Preferably, the rate of evaporation of the compound of Formula 1 on layer 104 ranges from 0.05 to 1 Å/s. More preferably, the rate of evaporation of the compound of Formula 1 on layer 104 ranges from 0.1 to 0.5 Å/s. The substrate temperature of layer 104 ranges from room temperature to 250° C., and more preferably the substrate temperature of layer 104 ranges from room temperature to 100° C. In one embodiment of the invention, film 110 is deposited by evaporation through a shadow mask to isolate the devices, thereby reducing leakage currents. A shadow mask is a patterned shield that exposes only a defined pattern on a surface to an incident beam. The thickness of film 110 ranges from 5 to 200 nm. Preferably, the thickness of film 110 ranges from 10 to 100 nm. More preferably, the thickness of film 110 ranges from 20 to 60 nm.

A source electrode 112 and a drain electrode 114 are then evaporated through a shadow mask, producing FET device 100. The channel length of FET device 100 can range from 2 to 2000 µm. Film and electrode patterning can be performed by using additive photolithography, subtractive photolithography, printing, micro contact printing, or pattern coating.

In one embodiment of the invention, electrodes 112 and 114 comprise gold. In other embodiments, electrodes 112 and 114 can comprise other conductive metal, organic conductive polymers or polymeric materials. For example, electrodes 112 and 114 can comprise carbon nanotubes (single wall or multi-wall carbon nanotubes); a mixture of polyaniline, dinonyinaphthalene sulfonic acid (DNNSA), and carbon nanotubes; or aluminum, barium, calcium, chromium, silver, nickel, palladium, platinum, titanium, doped polyaniline, or poly(3,4-ethylenedioxythiophene)/poly(styrene sulfonate) (PEDOT:PSS). In addition, alloys, combinations, and multilayers of these materials may also be used.

While the above section describes specific routes for the fabrication of a 'top contact' transistor, any fabrication method that produces substantially the same device geometry can be used. Alternate FET device geometries can also be used, one example of which is the 'bottom contact' geometry wherein the semiconductor is evaporated onto pre-patterned source/drain electrodes.

Characterization of FET devices provided by the invention, can be performed as follows:

Linear regime ($V_g <= V_{sd}$) mobility is calculated according to the equation:

$$\mu_{lin} = (L/WC_iV_{sd})(dI_d/dV_g)$$  Equation 1 where $I_d$ is the drain current, $V_g$ is gate voltage, $V_{sd}$ is source-drain voltage, L is channel length, W is channel width, and $C_i$ is capacitance per unit area of the gate insulator. $C_i$ is in units F/cm² and is calculated according to the following formula:

$$C_i = (\in_o \in/t)(10^{-4})$$  Equation 2 where $\in_0$ is the permittivity constant, $\in$ is the dielectric constant of the gate insulator, and t is the thickness of the insulator layer.

Saturation regime ($V_g >= V_{sd}$) mobility is calculated according to the equation:

$$\mu_{sat} = (2 * L * (d\sqrt{I_d}/dV_g)^2)/(W * C_i)$$  Equation 3

Threshold voltage, $V_t$, is measured in the saturation regime. The square root of $I_d$ is plotted versus $V_g$. Extrapolation of a line from the steepest portion of the curve to the x-axis provides $V_t$.

$I_{on}/I_{off}$ is measured at the highest $V_{sd}$ for the highest measured $V_g$ and dividing by the same $V_{sd}$ measured at $V_g=0$.

While the preferred embodiments of the invention have been illustrated and described, it will be clear that the invention is not limited to these embodiments only. Numerous modifications, changes, variations, substitutions, and equivalents will be apparent to those skilled in the art without departing from the spirit and scope of the invention as described in the claims.

EXAMPLES

Example 1

Synthesis of 5,5'-di(4-octyloxy-phenyl)-2,2'-bithiophene (Compound 4)

Example 1 illustrates a synthetic scheme for the preparation of phenylene-thiophene compounds of Formula 1. This example involves the synthesis of an exemplary compound, 5,5'-di(4-octyloxy-phenyl)-2,2'-bithiophene (Compound 4):

Compound 4

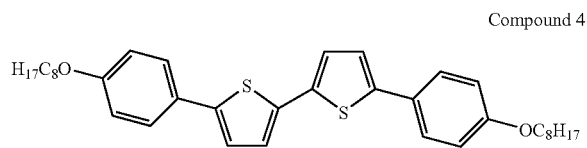

In a first step, 4-bromo-octyloxybenzene (Compound 6) was synthesized by the following reaction:

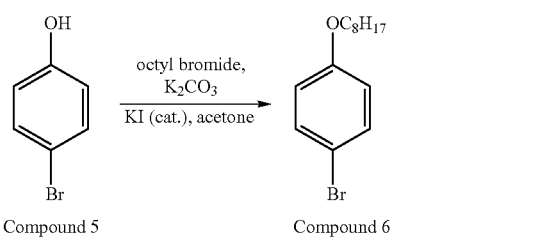

In a 1000 mL 3-neck flask, equipped with mechanism for stirring, 4-bromophenol (Compound 5) (25.0 g, 0.145 mol), octyl bromide (27.3 g, 0.141 mol), and potassium iodide (0.70 g (cat.)) were added. Thereafter, acetone (400 mL) was added and then potassium carbonate (60.0 g, 0.434 mol) was added portion-wise over 10 minutes. Nitrogen gas was then bubbled through the mixture for 20 minutes, prior to heating at reflux. After heating at reflux for 16 hours, the reaction mixture was cooled. Then, approximately two-thirds of the acetone was removed by rotary evaporation. Subsequently, n-hexane was added, and the solution was washed with water (3 times). The organic layer was dried by using MgSO₄, and the solvent was removed by rotary evaporation. Residual starting materials, octyl bromide and 4-bromophenol were removed by heating the crude product under vacuum (45 mtorr). The residual yellow oil, 4-bromo-octyloxybenzene (Compound 6, 31.52 g, 78%), was then used in the next step without further purification.

Compound 6 (4-bromo-octyloxybenzene) was further used for the preparation of 4-octyloxy-phenylboronic acid (Compound 7) by the following reaction:

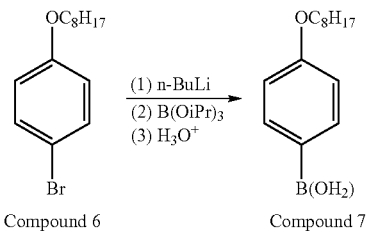

4-Bromo-octyloxybenzene (Compound 6, 31.5 g, 0.111 mol) was dissolved in 300 mL tetrahydrofuran. The solution was cooled to −78° C. in a cooling bath and n-butyllithium (55.3 mL of 2.5M solution, 0.138 mol) was added to it. After stirring for 25 minutes at −78° C., triisopropylborate (36.4 g, 0.194 mol) was added quickly with a syringe. The cooling bath was removed, and 90 minutes later, the solution was re-cooled to 0° C. 150 mL of a dilute HCl solution was added. After 30 minutes, ethyl ether was added to the reaction mixture and the organic layer was washed with water (2 times), dried with MgSO₄, and concentrated to provide an oil, which slowly crystallized over time. This crystallized product was re-crystallized once from acetonitrile to provide a colorless solid, 4-octyloxy-phenylboronic acid (Compound 7, 20.5 g, 74%).

Compound 7 (4-octyloxy-phenylboronic acid) was used to synthesize 5,5'-di(4-octyloxy-phenyl)-2,2'-bithiophene (Compound 4) by the following reaction:

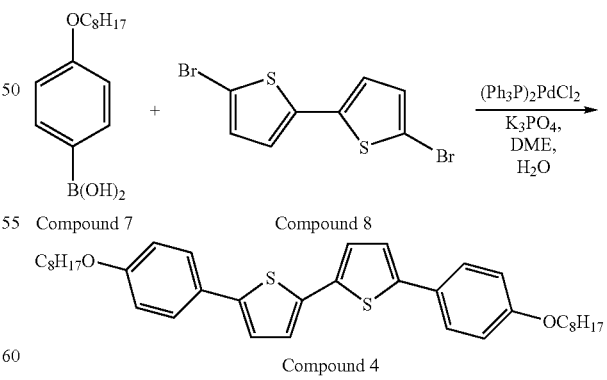

To a mixture of 4-octyloxy-phenylboronic acid (Compound 7) (12.0 g, 0.048 mol), 5,5'-dibromo-2,2'-bithiophene (Compound 8) (7.23 g, 0.022 mol), bis(triphenylphosphine) palladium (II) dichloride (0.39 g, 0.56 mmol), and potassium phosphate (15.3 g, 0.072 mol), 160 mL ethylene glycol dimethylether and 50 mL water were added. After heating for 4 hours at 70° C., the reaction mixture was cooled on an ice bath. The solids were filtered and washed with a small amount of chloroform. The solids were suspended in 600 mL water, stirred for 30 minutes, and then filtered. This washing procedure was repeated with methanol. Following two crystallizations from trifluorotoluene using decolorizing charcoal, 5,5'-di(4-octyloxy-phenyl)-2,2'-bithiophene (Compound 4) was isolated as yellow/orange crystals (10.34 g, 81%).

Example 2

Characterization of FET Devices

Example 2 provides results obtained after the characterization of FET devices that had a W/L ratio of 10, where W is the channel width and L is the channel length.

An FET device was fabricated in a similar manner as described in conjunction with FIG. 1. Thereafter, the FET device was characterized. Properties of the FET device were measured by using an Agilent 4155C™ Semiconductor Parameter Analyzer interfaced with a probe station.

Measurements were made under ambient conditions, with no special precautions taken to control temperature, or to exclude light or air. Reported values are the average values observed for eight different devices.

The following results were obtained from the above-mentioned characterization (temperature of the substrate=30° C.):
mobility (sat)=0.0545 cm$^2$/Vs
mobility (lin)=0.0228 cm$^2$/Vs
$I_{on}/I_{off}$=1.54×10$^5$
$V_t$(sat)=−2.4 V Additional measurements were made to determine if substrate temperature had a substantial effect on properties. The following results were obtained:

| T substrate (° C.) | mobility (sat) (cm$^2$/Vs) | $I_{on}/I_{off}$ | $V_t$ (sat) |
|---|---|---|---|
| 30 | 0.051 | 2.89E+05 | 0.8 |
| 70 | 0.065 | 2.66E+05 | 8.2 |
| 100 | 0.068 | 3.48E+05 | −0.7 |

The above results show that FET devices comprising compounds of Formula 1 have high mobilities and high on/off ratios. In addition, these values can be obtained without the need to heat the device substrate

What is claimed is:

1. An electronic device comprising:
    (a) an n-doped silicon wafer;
    (b) an adhesion layer disposed on one side of the silicon wafer;
    (c) a gate electrode disposed on the adhesion layer;
    (d) a gate insulator layer disposed on the other side of the silicon wafer;
    (e) a semiconductor layer disposed on the gate insulator layer, wherein the semiconductor layer comprises one or more compounds represented by Formula 1:

Formula 1

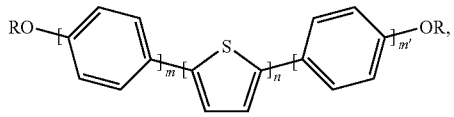

where R is selected from substituents comprising 2-20 carbon atoms, wherein the substituents are selected from substituted or unsubstituted alkyl groups, substituted or unsubstituted alkenyl groups, and substituted or unsubstituted alkynyl groups;
    n is an integer selected from 2 through 6; and
    m and m' are integers selected independently from 1 through 3; and
    (f) a source electrode and a drain electrode disposed on the semiconductor layer.

2. The electronic device of claim 1, wherein n is equal to 2, m is equal to 1, m' is equal to 1 and R is an unsubstituted alkyl group comprising 8 carbon atoms.

3. The electronic device of claim 1, wherein the electronic device is a thin film transistor or a field-effect transistor.

4. The electronic device of claim 1, wherein the gate insulator comprises a polymer selected from the group consisting of fluorinated para-xylene, fluoropolyarylether, fluorinated polyimide, polystyrene, poly (α-methyl styrene), poly(α-vinylnaphthalene), poly(vinyltoluene), polyethylene, cis-polybutadiene, polypropylene, polyisoprene, poly(4-methyl-1-pentene), poly(tetrafluoroethylene), poly(chlorotrifluoroethylene), poly(2-methyl-1,3-butadiene), poly(p-xylylene), poly[1,1-(2-methyl propane), poly(cyclohexyl methacrylate), poly(chlorostyrene), poly(2,6-dimethyl-1,4-phenylene ether), polyisobutylene, poly(vinyl cyclohexane), poly(arylene ether), polyphenylene, polypropylene, copolymers of tetrafluoroethylene and dioxoles such as 2,2-bistrifluoromethyl 5 4,5-difluoro-1,3-dioxole, fluoropolymers, fluoroepoxy polymers, fluorosilane, fluoroacrylic polymers, poly(dimethyl)siloxane and its copolymers, poly(ethylene/tetrafluoroethylene), poly (ethylene/chlorotrifluoroethylene), fluorinated ethylene/propylene copolymers, polystyrene-co-a-methyl styrene, ethylene/ethyl acrylate copolymers, poly(styrene/butadiene), poly(styrene/2,4 dimethylstyrene), polypropylene-co-1-butene, polyvinylalcohol, polyvinylphenol, polymethylmethacrylate, cyanoethylated polysaccharides, polyvinylidenefluoride, polyurethane polymers, poly(vinyl chloride/vinylacetate) polymers, poly(4-methylstyrene), and poly(1,3-butadiene).

5. The electronic device of claim 1, wherein the gate electrode comprises an organic conductive polymer selected from the group consisting of doped polyaniline and poly(3,4-ethylenedioxythiophene)/poly-(styrene sulfonate), or a conductive metal selected from the group consisting of gold, aluminum, chromium, nickel, palladium, platinum, tantalum, and titanium.

6. The electronic device of claim 1, wherein the source and drain electrodes comprise: a metal selected from the group consisting of gold, aluminum, barium, calcium, chromium, silver, nickel, palladium, platinum, and titanium; an organic conductive polymer and carbon nanotubes; a mixture of polyaniline, dinonylnaphthalene sulfonic acid (DNNSA), and carbon nanotubes; doped polyaniline; or poly(3,4-ethylenedioxythiophene)/poly(styrene sulfonate) (PEDOT:PSS).

7. An electronic device comprising
    (a) an n-doped silicon wafer;
    (b) an adhesion layer disposed on one side of the silicon wafer;
    (c) a gate electrode disposed on the adhesion layer;
    (d) a gate insulator layer disposed on the other side of the silicon wafer;
    (e) a source electrode and a drain electrode disposed on the gate insulator layer; and
    (f) a semiconductor layer disposed on the gate insulator layer and the source and drain electrodes, wherein the semiconductor layer comprises one or more compounds represented by Formula 1:

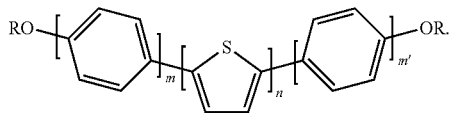

Formula 1 where R is selected from substituents comprising 2-20 carbon atoms, wherein the substituents are selected from substituted or unsubstituted alkyl groups, substituted or unsubstituted alkenyl groups, and substituted or unsubstituted alkynyl groups;

n is an integer selected from 2 through 6; and m and m' are integers selected independently from 1 through 3.

8. The electronic device of claim 7, wherein the electronic device is a thin film transistor or a field-effect transistor.

9. The electronic device of claim 7, wherein n is equal to 2, m is equal to 1, m' is equal to 1 and R is an unsubstituted alkyl group comprising 8 carbon atoms.

10. The electronic device of claim 7, wherein the gate insulator comprises a polymer selected from the group consisting of fluorinated para-xylene, fluoropolyarylether, fluorinated polyimide, polystyrene, poly (cc-methyl styrene), poly (oc-vinylnaphthalene), poly(vinyltoluene), polyethylene, cis-polybutadiene, polypropylene, polyisoprene, poly(4-methyl-1-pentene), poly(tetrafluoroethylene), poly(chlorotrifluoroethylene), poly(2-methyl-1,3-butadiene), poly(p-xylylene), poly[1,1-(2-methyl propane), poly(cyclohexyl methacrylate), poly(chlorostyrene), poly(2,6-dimethyl-1,4-phenylene ether), polyisobutylene, poly(vinyl cyclohexane), poly(arylene ether), polyphenylene, polypropylene, copolymers of tetrafluoroethylene and dioxoles such as 2,2-bistrifluoromethyl 5 4,5-difluoro-1,3-dioxole, fluoropolymers, fluoroepoxy polymers, fluorosilane, fluoroacryclic polymers, poly(dimethyl)siloxane and its copolymers, poly(ethylene/tetrafluoroethylene), poly (ethylene/chlorotrifluoroethylene), fluorinated ethylene/propylene copolymers, polystyrene-co-a-methyl styrene, ethylene/ethyl acrylate copolymers, poly (styrene/butadiene), poly(styrene/2,4 dimethylstyrene), polypropylene-co-1-butene, polyvinylalcohol, polyvinylphenol, polymethylmethacrylate, cyanoethylated polysaccharides, polyvinylidenefluoride, polyurethane polymers, poly(vinyl chloride/vinylacetate) polymers, poly(4-methylstyrene), and poly(1,3-butadiene).

11. The electronic device of claim 7, wherein the gate electrode comprises an organic conductive polymer selected from the group consisting of doped polyaniline and poly(3,4-ethylenedioxythiophene)/poly-(styrene sulfonate), or a conductive metal selected from the group consisting of gold, aluminum, chromium, nickel, palladium, platinum, tantalum, and titanium.

12. The electronic device of claim 7, wherein the source and drain electrodes comprise: a metal selected from the group consisting of gold, aluminum, barium, calcium, chromium, silver, nickel, palladium, platinum, and titanium; an organic conductive polymer and carbon nanotubes; a mixture of polyaniline, dinonylnaphthalene sulfonic acid (DNNSA), and carbon nanotubes; doped polyaniline; or poly(3,4-ethylenedioxythiophene)/poly(styrene sulfonate) (PEDOT:PSS).

* * * * *